United States Patent [19]
Pietsch et al.

[11] 3,969,348
[45] July 13, 1976

[54] PROCESS FOR THE MANUFACTURE OF 6-METHYL-3,4-DIHYDRO-1,2,3-OXATHIAZIN-4-ONE-2,2-DIOXIDE

[75] Inventors: Hartmut Pietsch, Hofheim, Taunus; Karl Clauss, Rossert, Taunus; Erwin Schmidt, Kelkheim, Taunus; Harald Jensen, Frankfurt am Main, all of Germany

[73] Assignee: Hoechst Aktiengesellschaft, Frankfurt am Main, Germany

[22] Filed: July 16, 1975

[21] Appl. No.: 596,231

[30] Foreign Application Priority Data
July 18, 1974   Germany............................ 2434562

[52] U.S. Cl............................................. 260/243 R
[51] Int. Cl.² ...................................... C07D 291/06
[58] Field of Search ................................ 260/243 R

[56] References Cited
UNITED STATES PATENTS

| | | | |
|---|---|---|---|
| 3,926,976 | 12/1975 | Clauss et al.......................... | 260/243 |
| 3,926,981 | 12/1975 | Clauss et al.......................... | 260/243 |

*Primary Examiner*—John M. Ford
*Attorney, Agent, or Firm*—Curtis, Morris & Safford

[57] ABSTRACT

6-Methyl-3,4-dihydro-1,2,3-oxathiazin-4-one-2,2-dioxide or the nontoxic salts thereof is prepared by reacting 6-methyl-2,3-dihydro-1,3-oxazin-2,4-dione-3-sulfo-fluoride of the formula

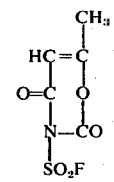

with at least 1 mole water per mole of fluoride to obtain acetoacetamide-N-sulfo-fluoride with splitting off of $CO_2$, treating the acetoacetamide-N-sulfofluoride with an aqueous and/or alcoholic base and isolating the oxathiazinone or the salts thereof.

6 Claims, No Drawings

PROCESS FOR THE MANUFACTURE OF 6-METHYL-3,4-DIHYDRO-1,2,3-OXATHIAZIN-4-ONE-2,2-DIOXIDE

This invention relates to a process for the manufacture of 6-methyl-3,4-dihydro-1,2,3-oxythiazin-4-one-2,2-dioxide which is distinguished by a very sweet taste and can, therefore, be used as a sweetener.

Oxazin-diones, for example 3-phenyl-5,6-benzodihydro-1,3-oxazin-2,4-dione (T.Kato, Kagaku No Rijoiki, Zokan 1970, 92 (Pt.2)203, Japanese) or 6-methyl-2,3-dihydro-1,3-oxazin-2,4-dione (V. I. Gunar et al., Izv.Akad.Nauk.S.S.S.R., Ser.Khim, (1965) page 1076), are known stable compounds.

It has been found that under the action of water the ring of 6-methyl-2,3-dihydro-1,3-oxazin-2,4-dione-3-sulfofluoride of formula I is opened with splitting off of $CO_2$ whereby acetoacetamide-N-sulfofluoride II is obtained which can be transformed into 6-methyl-3,4-dihydro-1,2,3-oxathiazin-4-one-2,2-dioxide III a known sweetener according to the following reaction scheme:

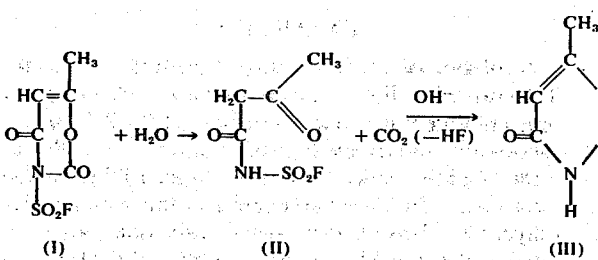

It is, therefore, the object of the present invention to provide a process for the manufacture of 6-methyl-3,4-dihydro-1,2,3-oxathiazin-4-one-2,2-dioxide and its nontoxic salts, which comprises reacting 6-methyl-2,3-dihydro-1,3-oxazin-2,4-dione-3-sulfofluoride of the formula I

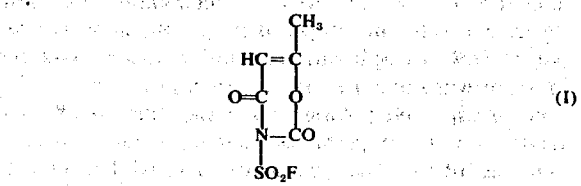

with at least 1 mole water per mole of compound I to obtain acetoacetamide-N-sulfofluoride of formula II and $CO_2$ and treating the acetoacetamide-N-sulfofluoride II with an aqueous and/or alcoholic base to obtain 6-methyl-3,4-dihydro-1,2,3-oxathiazine-4-one-2,2-dioxide I and the salts thereof.

The compound of formula I can be prepared in simple manner by the method described in our application Ser. No. 596,227 filed concurrently herewith by reacting fluorosulfonyl isocyanate (FSI) with diketene, acetoacetic acid, acetoacetyl chloride, or isopropenyl acetate.

Owing to the fact that the compound of formula I is only very sparingly soluble in water, the ring opening is preferably carried out in the presence of a dissolving intermediary, for example inert solvents that are wholly or partially miscible with water such as alcohols, for example methanol, ethanol, or isopropanol; ketones, for example acetone or butanone; ethers, for example dimethoxy-ethane, dioxane, or tetrahydrofurane. Solvents which are immiscible or little miscible with water only can also be used as a dispersion in water, for example chlorohydrocarbons, esters such as ethyl acetate, ethers such as diethyl ether, di-isopropyl ether or hydrocarbons having more than 4 carbon atoms.

To open the ring or bring about decarboxylation of compound I 1 mole water is required per mole of compound I. It proved advantageous, however, above all for increasing the reaction speed, to use a higher amount of water than stoichiometrically required, for example up to 20 moles or more, preferably 2 to 10 moles, the upper limit being determined by the fact that a sufficient solubility of compound I in the solvent diluted with water is ensured. With the use of solvents little miscible with water, which are used in the form of dispersions in water, this condition is generally complied with and, therefore, in this case the upper limit for the amount of water used is essentially determined by technical considerations, in the first place recovery of compounds II or III from the water used. Hence, an amount of about 1 liter of water per mole of compound I will generally not be exceeded.

The decarboxylation according to the above scheme is preferably carried out at a temperature of from 0° to +60°C, more preferably 10° to 30°C.

Compound II obtained in this manner can be transformed into the sweetener of formula III or the salts thereof by a treatment with bases, for example as described in U.S. Pat. No. 3,689,486.

The cyclization can be effected in an especially simple manner by 1. mixing aqueous solutions of the acetoacetamide-N-sulfofluoride obtained as intermediate with aqueous solutions, dispersions or suspensions of the bases used or
2. mixing a solution of the acetoacetamide-N-sulfofluoride in an organic solvent, for example methanol, ethanol, isopropanol, acetone, dimethoxyethane, or tetrahydrofurane, with a solution of the base used in an alcohol, for example methanol, ethanol, or isopropanol or a mixture thereof with water.

Owing to the fact that the salts of the oxathiazinone obtained with inorganic cations, above all the alkali metal salts, and more especially the potassium salt of 6-methyl-3,4-dihydro-1,2,3-oxa-thiazin-4-one-2,2-dioxide, are sparingly soluble in alcohols, the cyclization to the oxathiazinone can be effected in an especially simple and advantageous manner in an alcohol, for example methanol, ethanol or isopropanol, or in mixtures thereof containing less than 50% by weight, preferably less than 20% by weight of water, with the addition of bases. The oxathiazinone salt of an inorganic base can be isolated practically quantitatively. From the salt the free oxathiazinone can be prepared in known manner without difficulty. It is particularly advantageous to add methanolic potassium hydroxide, potassium methylate, or potassium carbonate solution to a solution of the crude acetoacetamide-N-sulfofluoride in methanol. The potassium salt of 6-methyl-3,4-dihydro-1,2,3-oxathiazin-4-one-2,2-dioxide separates in the form of crystals and can be filtered off with suction whereas the potassium fluoride formed essentially remains in solution so that it can be readily separated from the oxathiazine derivative. The ring formation in methanolic solution is, therefore, a preferred embodiment since the oxathiazinone obtained is substantially free from fluoride, which is of extreme importance when the compound is used as sweetener.

Suitable bases for the cyclization are, for example, hydroxides, acid and neutral carbonates of alkali metals, alkali metal alcoholates, calcium hydroxide and oxide, barium hydroxide and oxide, ammonia, amines such as methyl amine, ethyl amine, dimethyl amine, diethyl amine, trimethyl amine, triethyl amine, and the like, potassium hydroxide, potassium methylate and potassium carbonate being preferred.

The cyclization is suitably carried out at a temperature of from 5° to 85°C, the optimum temperature depending in each case on the type of the base used. With a weak base, for example $NaHCO_3$, in water the reaction mixture must be heated to 40° – 85°C, while with a strong base such as methanolic alkali metal hydroxide solution the ring closes at a temperature of from 5° to 50°C.

It is not necessary to perform the two stages, i.e. ring opening or decarboxylation of compound I and cyclization of compound II separately. It proved advantageous directly to add compound I to an aqueous or water-containing solution or dispersion of one of the aforesaid bases and to obtain in this manner the salts of the oxathiazinone dioxide III used as sweetener. When the two stages are combined, the two reactions take place at a temperature of about 0° to 85°C. In this range the acetoacetamide-N-sulfofluoride formed as intermediate is not subject to secondary reactions with water or alcohols but directly reacts further with the base to the oxathiazinone dioxide III.

For further purification, if any, the crude potassium salt of the oxathiazinone can be recrystallized from boiling water, optionally with addition of charcoal and filtering aids and obtained in a pure state. An addition of calcium hydroxide promotes the separation of traces of fluoride as insoluble $CaF_2$, which can be readily separated from the solution.

A control of purity of the 6-methyl-3,4-dihydro-1,2,3-oxathiazin-4-one-2,2-dioxide and of its salts is possible by simple UV measurement in dilute solution as the product shows a high absorption maximum at 225 – 228 nm with $\epsilon = $ about $1.10^4$.

The following examples illustrate the invention.

EXAMPLE 1

10 ml water were added while stirring to a solution of 21.0 g (0.1 mole) 6-methyl-2,3-dihydro-1,3-oxazin-2,4-dione-3-sulfofluoride melting at 85° – 86°C in 40 ml dimethoxyethane. When the evolution of gas was terminated, the solvent was distilled off under reduced pressure, the residue was taken up in water and 50 ml 4N sodium hydroxide solution was added dropwise at 20° – 30°C. The reaction mixture was acidified with 15 ml concentrated hydrochloric acid and extracted with ethyl acetate. By distillation of the ethyl acetate 16.0 g of crystalline 6-methyl-3,4-dihydro-1,2,3-oxathiazin-4-one-2,2-dioxide melting at 117° – 120°C were obtained in the form of colorless crystals. By treating the methanolic solution of the acid with methanolic potassium hydroxide solution 18.1 g of pure potassium salt were obtained, corresponding to 90% of the theory.

EXAMPLE 2

4.2 g (20 mmoles) 6-methyl-2,3-dihydro-1,3-oxazin-2,4-dione-3-sulfofluoride melting at 85° – 86°C were introduced in portitions into 25 ml 2N methanolic potassium hydroxide solution prepared from KOH of 85% strength and methanol. With the evolution of gas a colorless potassium salt precipitated. The reaction mixture was stirred for a further 30 minutes at 30° – 40°C, the crystals were filtered off with suction and washed with methanol. 3.1 g (15.5 mmoles) of the potassium salt of 6-methyl-3,4-dihydro-1,2,3-oxathiazin-4-one-2,2-dioxide containing less than 0.1% by weight fluoride were obtained.

Yield 75% of theory.

EXAMPLE 3

A solution of 21.0 (0.1 mole) 6-methyl-2,3-dihydro-1,3-oxazin-2,4-dione-3-sulfofluoride in 100 ml methylene chloride was added dropwise at 20° – 25°C to 100 ml of water and the methylene chloride was distilled off under slightly reduced pressure. 20 ml 10N potassium hydroxide solution were added and the 6-methyl-3,4-dihydro-1,2,3-oxathiazin-4-one-2,2-dioxide was isolated as described in Example 15 by acidification with 0.2 mole mineral acid and extraction with ethyl acetate.

Yield 85% of theory.

EXAMPLE 4

A solution of 10.5 g (50 mmoles) 6-methyl-2,3-dihydro-1,3-oxazin-2,4-dione-3-sulfofluoride in 40 ml methylene chloride was added dropwise, while stirring and cooling to 0°C, to 50 ml 2N methanolic potassium hydroxide solution, prepared from potassium hydroxide of 86% strength and methanol, and stirring of the mixture was continued for 30 minutes at 30° – 40°C. The precipitated potassium salt was filtered off with suction and thoroughly washed with methanol. 7.6 g (38 mmoles) of the potassium salt of 6-methyl-3,4-dihydro-1,2,3-oxathiazin-4-one-2,2-dioxide were obtained in the form of colorless crystals substantially free of fluoride (less than 0.1% by weight).

Yield 75% of theory.

EXAMPLE 5

While cooling with ice, 21.0 g (0.1 mole) 6-methyl-2,3-dihydro-1,3-oxazin-2,4-dione-3-sulfofluoride were introduced into 110 ml 2N sodium hydroxide solution. With temperature increase $CO_2$ developed. After standing for 30 minutes at room temperature, the reaction mixture was acidified with 10 ml concentrated hydrochloric acid and extracted with ethyl acetate. After evaporation of the solvent 13.2 g (0.081 mole) 6-methyl-3,4-dihydro-1,2,3-oxathiazin-4-one-2,2-dioxide were obtained, which was recrystallized from ethyl acetate/chloroform and then melted at 123° – 124°C.

Yield 81% of theory.

EXAMPLE 6

A solution of 21.0 g (0.1 mole) 6-methyl-2,3-dihydro-1,3-oxazin-2,4-dione-3-sulfofluoride in 100 ml acetone was stirred with 10 ml water until the evolution of gas was terminated. Milk of lime containing 0.11 mole $Ca(OH)_2$ was added and the acetone was distilled off under reduced pressure. After addition of a filtering aid the precipitated $CaF_2$ was filtered off, the aqueous solution of the calcium salt of 6-methyl-3,4-dihydro-1,2,3-oxathiazin-4-one-2,2-dioxide was acidified with concentrated hydrochloric acid and the free acid was extracted with ethyl acetate. The product melted at 123° – 124°C.

Yield 12.7 g, corresponding to 78% of the theory.

EXAMPLE 7

10 ml water were added in portions to a solution of 10.5 g (50 mmoles) 6-methyl-2,3-dihydro-1,3-oxazin-2,4-dione-3-sulfofluoride melting at 85° – 86°C in 50 ml dimethoxyethane. During the course of reaction 1150 ml $CO_2$ were split off. After distillation under reduced pressure of the limpid colorless solution, 9.3 g colorless crystals melting at 80° – 85°C were obtained. When the crystals were recrystallized from chloroform, 7.8 g of pure acetoacetamide-N-sulfofluoride melting at 87° – 88°C were obtained (cf. South African Specification No. 73/9560). The product was identified by mixed melting point and comparison of the IR spectra.

Yield 85% of theory.

The pure cyrstals were dissolved in 50 ml methanol and immediately thereafter 20 ml 5N methanolic KOH were added dropwise at 20°C. 8.1 g (40.4 mmoles) of the potassium salt of 6-methyl-3,4-dihydro-1,2,3-oxathiazin-4-one-2,2-dioxide were obtained which, after washing with methanol, contained less than 0.1% fluoride.

Yield 81% of theory.

EXAMPLE 8

A solution of 21.0 g (0.1 mole) 6-methyl-2,3-dihydro-1,3-oxazin-2,4-dione-3-sulfofluoride in 80 ml acetone was stirred with 5.0 ml water until the evolution of gas had ceased. A mixture of 17 g (0.2 mole) sodium bicarbonate and 50 ml water was added in portions and the mixture was heated for 20 minutes at 55° – 60°C. After cooling to 0°C, the mixture was acidified with 20 ml concentrated hydrochloric acid and extracted with ethyl acetate. After distillation of the solvent, 14.0 g (86 mmoles) 6-methyl-3,4-dihydro-1,2,3-oxathiazin-4-one-2,2-dioxide melting at 118° – 120°C were isolated.

Yield 86% of theory.

EXAMPLE 9

21.0 g (0.1 mole) 6-methyl-2,3-dihydro-1,3-oxazin-2,4-dione-3-sulfofluoride were added in portions to a mixture of 50 ml tetrahydrofurane and 50 ml water. When the evolution of gas had ceased 19 ml concentrated aqueous ammonia solution were added dropwise at 20° – 30°C and the tetrahydrofurane was distilled off under reduced pressure. The free acid was isolated from the aqueous solution of the crude ammonium salt of 6-methyl-3,4-dihydro-1,2,3-oxathiazine-4-one-2,2-dioxide as described above by acidification with 20 ml concentrated hydrochloric acid and extraction with ethyl acetate.

Yield 82% of theory.

EXAMPLE 10

A solution of 21.0 g (0.1 mole) 6-methyl-2,3-dihydro-1,3-oxazin-2,4-dione-3-sulfofluoride in 50 ml ethyl acetate was vigorously stirred at 20° – 30°C with 25 ml water until the evolution of gas had ceased. 20.2 g (0.2 mole) triethylamine were added dropwise at 25° – 30°C and the mixture was heated for 15 minutes to 50°C while vigorously stirring. After cooling, the mixture was acidified with 25 ml concentrated hydrochloric acid at a temperature of 0° to 5°C, stirred and the ethyl acetate layer was separated. Extraction with 20 ml each of ethyl acetate was repeated twice and from the combined and dried ethyl acetate solutions 13.2 g (81 mmoles) 6-methyl-3,4-dihydro-1,2,3-oxathiazin-4-one-2,2-dioxide melting at 118° – 120°C were obtained after drying under reduced pressure.

Yield 81% of theory.

We claim:

1. A process for the manufacture of 6-methyl-3,4-dihydro-1,2,3-oxathiazin-4-one-2,2-dioxide or the nontoxic salts thereof, which comprises reacting 6-methyl-2,3-dihydro-1,3-oxazin-2,4-dione-3-sulfo-fluoride of fomrula I

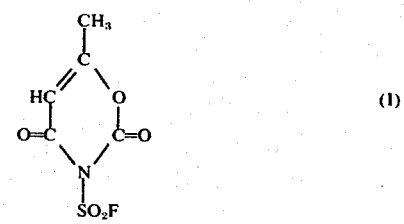

with at least one mole water per mole of fluoride to obtain acetoacetamide-N-sulfo-fluoride with splitting off of $CO_2$, treating the acetoacetamide-N-sulfofluoride with an aqueous or alcoholic base or combination thereof and isolating the oxathiazinone or the salts thereof.

2. The process of claim 1, wherein 1 to 20 and preferably 2 to 10 moles of water are used.

3. The process of claim 1, wherein the reaction is carried out in the presence of a dissolving intermediary.

4. The process of claim 1, wherein the reaction is carried out at a temperature of from 0° to 85°C.

5. The process of claim 1, wherein the acetoacetamide-N-sulfofluoride is treated with a base in alcoholic solution containing less than 50% by weight and preferably less than 20% by weight of water.

6. The process of claim 5, wherein a methanolic solution of potassium methylate, potassium hydroxide or potassium carbonate is used.

* * * * *